United States Patent [19]

Hall et al.

[11] 4,017,538

[45] Apr. 12, 1977

[54] ALKYL THIO SULFINYL AND SULFONYL OXAMIC COMPOUNDS, COMPOSITIONS AND METHODS OF USE

[75] Inventors: Charles M. Hall; John B. Wright, both of Kalamazoo, Mich.

[73] Assignee: The Upjohn Company, Kalamazoo, Mich.

[22] Filed: Oct. 1, 1975

[21] Appl. No.: 618,509

[52] U.S. Cl. .................. 260/518 R; 260/293.73; 260/326.2; 260/326.4; 260/465 D; 260/470; 260/501.1; 260/516; 260/518 A; 260/519; 260/578; 424/300; 424/304; 424/309; 424/319

[51] Int. Cl.² ............... C07C 101/78; A61K 31/24

[58] Field of Search .......... 260/518 R, 518 A, 519, 260/465 D, 465 F, 465 G, 501.1, 516; 424/317, 319, 304

[56] References Cited

UNITED STATES PATENTS

| | | | |
|---|---|---|---|
| 3,251,854 | 5/1966 | Sims | 260/518 R |
| 3,683,020 | 8/1972 | Luethi et al. | 260/518 R |
| 3,906,033 | 9/1975 | Biland et al. | 260/518 R |
| 3,926,993 | 12/1975 | Ishizumi et al. | 260/518 R |
| 3,966,965 | 6/1976 | Sellstedt et al. | 260/518 R |

*Primary Examiner*—Norman Morgenstern
*Attorney, Agent, or Firm*—Martin B. Barancik; Roman Saliwanchik

[57] ABSTRACT

It has now been discovered that novel compounds of the figure below and their pharmaceutical compositions are useful in the prophylactic treatment of sensitized humans and animals for allergy and anaphylactic reactions of a reagin or non-reagin mediated nature.

12 Claims, No Drawings

ALKYL THIO SULFINYL AND SULFONYL OXAMIC COMPOUNDS, COMPOSITIONS AND METHODS OF USE

BRIEF SUMMARY OF THE INVENTION

It has now been discovered that novel compounds of Formula I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention, there are provided compounds represented by Formula I and hereafter referred to as Group A $$\underset{R_1S}{\overset{(O)_n}{\underset{\phantom{.}}{\phantom{..}}}}\!\!\!\!\!\!\!\!\!\!\!\!\!\!\!\!\!\!\!\!\!\!\!\!\!\!\!\phantom{X}$$

(structure: benzene ring with Y at position 6, $R_1S(O)_n$ at position 5, X at position 3 or 4, and $-N(H)-C(O)-C(O)-OR$ at position 1)

where X is at the 3 or 4 position and is hydrogen or $$-\underset{H}{N}-\underset{\|}{\overset{O}{C}}-\underset{\|}{\overset{O}{C}}-OR;$$

Y is selected from the group consisting of hydrogen, alkyl of one to four carbon atoms, inclusive, alkoxy of one to four carbon atoms, inclusive, halo, hydroxy, cyano, nitro, trifluoromethyl, $$C\overset{\nearrow O}{\underset{\searrow}{-}}OD$$

wherein D is selected from the group consisting of hydrogen, alkyl of one to four carbon atoms, inclusive, and physiologically acceptable metal or amine cation;

$$\overset{O}{\underset{\|}{C}}N\underset{R_3}{\overset{R_2}{\diagdown}}\quad\text{and}\quad N\underset{R_3}{\overset{R_2}{\diagdown}}$$

wherein $R_2$ and $R_3$ are the same or different and are selected from the group consisting of hydrogen and alkyl of one to six carbon atoms, inclusive, and $R_2$ and $R_3$ when taken together with the nitrogen atom to which they are attached form a saturated heterocyclic ring having from four to six carbon atoms, inclusive;

R is selected from the group consisting of hydrogen, alkyl of one to eight carbon atoms, inclusive, $$-(-CH_2-)_m-\!\!\bigcirc$$

wherein m is 0, 1 or 2, and physiologically acceptable metal or amine cation;

$R_1$ is selected from the group consisting of hydrogen, alkyl of one to six carbon atoms, inclusive, cycloalkyl of five to six carbon atoms, inclusive; and n is 0, 1 or 2.

A further group of compounds hereafter referred to as Group B are compounds of Group A wherein R is selected from the group consisting of hydrogen, alkyl of one to six carbon atoms, inclusive, phenyl, or a physiologically acceptable metal or amine cation.

A further group of compounds hereafter referred to as Group C are compounds of Group B wherein Y is selected from the group consisting of hydrogen, alkyl of one to three carbon atoms, inclusive, alkoxy of one to three carbon atoms, inclusive, halo, hydroxy, cyano, nitro, trifluoromethyl, $$C\overset{\nearrow O}{\underset{\searrow}{-}}OD$$

wherein D is selected from the group consisting of hydrogen, alkyl of one to three carbon atoms, inclusive, and a physiologically acceptable metal or amine cation;

$$\overset{O}{\underset{\|}{C}}N\underset{R_3}{\overset{R_2}{\diagdown}}\quad\text{and}\quad N\underset{R_3}{\overset{R_2}{\diagdown}}$$

wherein $R_2$ and $R_3$ are the same or different and are selected from hydrogen and alkyl of one to three carbon atoms, inclusive.

A still further group of compounds hereafter referred to as Group D are compounds of Group C wherein X is at the 3 position, Y is selected from the group consisting of hydrogen, alkyl of one to three carbon atoms, inclusive, alkoxy of one to three carbon atoms, inclusive, fluoro, chloro, bromo, cyano, trifluoromethyl and $$C\overset{\nearrow O}{\underset{\searrow}{-}}OD,$$

$R_1$ is selected from the group consisting of hydrogen and alkyl of one to four carbon atoms, inclusive.

Another group of compounds hereafter referred to as Group E are compounds of Group D wherein R is selected from the group consisting of hydrogen, alkyl of one to four carbon atoms, inclusive, and a physiologically acceptable metal or amine cation, Y is at the 2 or 5 position, $$R_1S^{(O)_n}$$

is at the 2 or 5 position.

Groups A, B, C, D, and E are each individually disclosed with n having the separate limitation of 0, 1 or 2.

As employed in the above disclosure and throughout the specification and claims, the phrase "alkyl of one to eight carbon atoms, inclusive" includes methyl, ethyl, propyl, butyl, pentyl, hexyl, heptyl, octyl and isomers thereof. Illustrative examples of isomers are isopropyl, tert-butyl, neopentyl, 2,2-dimethylbutyl, isoheptyl and 2,2,4-trimethylpentyl. Alkyl of a smaller number of carbon atoms has a similar scoping. The term "halogen" includes fluoro, chloro, bromo and iodo.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

The compounds of the invention can be prepared by methods known in the art. The appropriate Y-substituted aminobenzenethiol starting material is carried throughout the further synthetic steps as a compound wherein $R_1$ is hydrogen or is converted to an alkyl, cycloalkyl, or phenyl group by a standard alkylation reaction, preferably prior to the conversion of the amino grouping to the oxamate grouping. After conversion of the thiol grouping to a non-hydrogen $R_1$, the aminobenzenethiol compound is converted by standard reactions to the benzenethiooxamate. The oxamate may be then transesterified to any desired ester under standard conditions. The ester is then converted to the oxamic acid or metal or amine salt by the usual reactions. Any oxidation to a sulfoxide, $n=1$, or a sulfone, $n=2$, can occur at any of the above steps but it is preferably undertaken after preparation of the oxamate ester. Standard oxidation reaction conditions and reagents are employed.

When a compound wherein X is

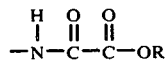

is desired, the appropriately Y-substituted diaminobenzenethiols are employed in the above reaction scheme. The diaminobenzenethiols and readily prepared by standard reduction techniques of dinitrobenzenethiols.

Those dioxamates which require a 3,5-diaminobenzenethiol as the starting material are readily prepared by nitration of a p-$R_1$ thiophenol with nitric acid followed by reduction of the nitro groups to amino. A Y substituent may be placed upon the phenyl at the dinitro or diamino stage.

Following are illustrative examples of some aminobenzenethiol and some dinitrobenzenethiol compounds known in the literature. This list is not intended to be exhaustive.

TABLE I

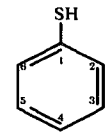

| | |
|---|---|
| 2-NH$_2$, 4-Br | 4-NH$_2$, 2-F |
| 2-NH$_2$, 5-Br | 4-NH$_2$, 3-F |
| 4-NH$_2$, 2-Br | 4-NH$_2$, 3-I |
| 2-NH$_2$, 4-Cl | 2-NH$_2$, 4-MeO |
| 4-NH$_2$, 2-Cl | 2-NH$_2$, 5-NO$_2$ |
| 4-NH$_2$, 3-Cl | 4-NH$_2$, 3-Br |
| 2-NH$_2$, 5-EtO | 2-NH$_2$, 5-Et$_2$N |
| 2-NH$_2$, 5-F | 3-NH$_2$, 4-propyl |
| 2-Sec-Butyl-4,6-diNO$_2$ | |
| 4-t-Butyl-2-6-DiNO$_2$ | |
| 2-Cl-4,6-diNO$_2$ | |
| 2,4-diNH$_2$ | |
| 2,6-diNO$_2$ | |
| 5-EtO-2,4-diNO$_2$ | |
| 5-MeO-2,4-diNO$_2$ | |
| 2-Br-4,6-diNO$_2$ | |
| 3-Br-2-Cl-4,6-diNO$_2$ | |
| 2-Cl-2,6-diNO$_2$ | |
| 5-Cl-2,6-diNO$_2$ | |

The thiol grouping is converted to other $SR_1$ groups by a standard alkylation reaction. These reactions are run in organic solvents under basic conditions. Examples of typical organic solvents are lower alcohols, ethers, cyclic or acyclic, amides, sulfoxides. Examples of these solvents are methanol, ethanol, propanol, tetrahydrofuran, dioxane, dimethylformamide and dimethylsulfoxide. Bases which can be employed are sodium or potassium hydroxide in ethanol, lithium amides, alkali metal alkoxides. Typical alkylating agents which can be employed are the halo $R_1$ compounds, particularly the chloro or bromo, for example, ethyl chloride, isobutyl bromide, cyclohexyl bromide, etc. The temperature of the reaction depends upon the reaction kinetics desired. Temperatures of from about 0° C. to the reflux temperature of the system can be employed. This alkylation is conveniently carried out at the nitro or amino stage of the synthetic pathway.

If a dinitro compound is the initial starting material, the reduction of nitro to an amino grouping can be easily effected by catalytic means such as Raney Nickel, palladium on charcoal or platinum in the presence of hydrogen. Additionally, chemical means are also available for reduction of nitro to amino, for example, stannous chloride in concentrated hydrochloric acid, and iron in acetic acid with ethanol.

The amino grouping is converted to an oxamate group by reacting with an oxalyl halide preferably ethyl oxalyl chloride in a suitable solvent and base to form the oxamate. An alternative method of preparing the oxamate is to react the amino compound with a dialkyl oxalate, preferably diethyl oxalate, in neat solution or with an additional solvent if necessary at a temperature ranging from about 25° C. to about reflux temperature of the system. When using an alkyl oxalyl halide, reaction is carried out in base and solvent at standard conditions. Examples of suitable solvents are dimethylformamide, dioxane, and tetrahydrofuran. Appropriate bases include triethylamine, N-methylmorpholine, dimethylpiperazine, and N-methylpiperidine. When the dialkyl oxalate is employed, the amino starting material is heated together with the dialkyl oxalate or an additional solvent such as a xylene or diphenyl ether if desired, thereby forming the oxamate. The temperature is from about 25° C. to the reflux temperature of the system.

At this point of the synthetic pathway, the oxamate can be transesterified to other esters and/or converted to the acid by hydrolysis and thence to the metal or amine salts by standard methods.

The oxamate is readily converted to the oxamic acid by using dilute base such as sodium hydroxide, potassium hydroxide or potassium carbonate at temperatures ranging from about 25° to about 100° C., followed by addition of acid. The alkaline metal salts of the oxamate may be soluble in aqueous medium or relatively insoluble. If soluble in aqueous medium, the pH is adjusted with acid and the resulting precipitate is collected. If the alkaline metal salt is insoluble in aqueous medium the precipitate per se can be collected and then heated in aqueous acid to an appropriate temperature, collecting the mixture and isolating the desired diacid. The acid can then be easily converted to the metal or amine salt by contacting the acid with an equivalent of the desired amine or metal hydroxide and heating in a sufficient amount of water to effect solubilization. The crystalline salts can be precipitated by the addition of an organic solvent, for example, methanol.

The hydrolysis of the ester to the acid can be performed at the thio, sulfoxide or sulfone stage.

The oxidation of the thio compound can be carried out conveniently with standard reagents under standard conditions. Although the reaction can be conveniently executed at various stages of the synthetic pathway, it is preferably carried out at the oxamate stage. Solvents which can be employed are inert organic solvents such as halogenated alkanes, e.g., methylene chloride. The oxidizing agent employed is any peroxy agent which will not disrupt other features of the molecule. Examples of suitable peroxy agents are peroxybenzoic acids such as meta-chloroperoxybenzoic acid, peroxybenzoic acid, peracetic acid, hydrogen peroxide. In order to form the sulfoxide, one equivalent of the oxidizing agent should be used. The sulfone is formed when greater than two equivalents of the oxidizing agent are employed. If only the sulfoxide is desired, sodium metaperiodate can be used. The reaction is run at temperatures ranging from about 10° to about 40° C.

The starting material is referred to generally as Y-substituted. The Y substituent can be placed on the ring at various points of the synthetic pathway as well, depending upon the position of the desired Y substituent and the orientation directing effects of the other ring substituents.

Following are illustrative examples of compounds within the generic scope of this invention. These examples are not intended to be exhaustive or to limit the scope of the invention.

TABLE II

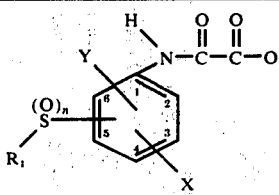

X is hydrogen, R is ethyl

| Y | SR₁ | n |
|---|---|---|
| H | 2-SH | 0 |
| H | 2-SH | 1 |
| H | 2-SH | 2 |
| 3-C₂H₅ | 2-SCH₃ | 0 |
| 4-CN | 2-SC₃H₇ | 1 |
| 5-CF₃ | 2-S-i-C₅H₁₁ | 1 |
| H | 2-S-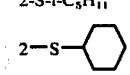 | 2 |
| 6-Cl | 2-S-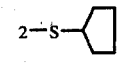 | 0 |
| 4-N(C₂H₅)(C₃H₇) | 2-SC₂H₅ | 1 |
| 2-OH | 3-SC₂H₅ | 0 |
| H | 3-S-t-C₄H₉ | 2 |
| 4-OC₄H₉ | 3-S-i-C₆H₁₃ | 2 |
| 5-NO₂ | | 1 |
| | 3-S-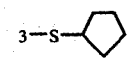 | |
| 6-CF₃ | 3-SH | 0 |
| 2C(=O)OH | 4-SCH₃ | 1 |
| 2-i-C₄H₉ | 4-S-i-C₄H₉ | 0 |
| H | 4-S-n-C₆H₁₃ | 1 |
| 3-F | | 1 |
| | 4-S-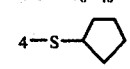 | |
| 3-NHCH₃ | 4-SC₃H₇ | 0 |
| 4-C(=O)N-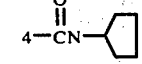 | 2-S-i-C₃H₇ | 2 |
| 3-C(=O)NHC₂H₅ | 4-SC₂H₅ | 2 |
| 5-C(=O)OC₂H₅ | 2-S-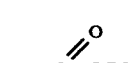 | 2 |
| 6-C(=O)N(C₂H₅)(C₆H₁₃) | 3-SC₅H₁₁ | 1 |
| 2-Br | 3-S-dimethylbutyl | 0 |
| 2-OCH₃ | | 1 |
| | 4-S-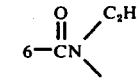 | |
| 3-CN | 4-S-i-C₅H₁₁ | 1 |
| 2-N-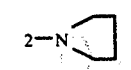 | 4-SCH₃ | 0 |

TABLE III

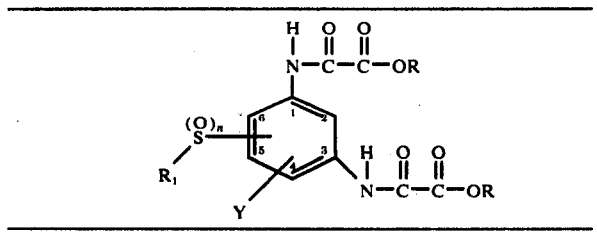

R is ethyl

| Y | SR₁ | n |
|---|---|---|
| H | 2-SH | 0 |
| 5-CH₃ | 2-SCH₃ | 1 |
| 5-i-C₃H₇ | 2-SC₃H₇ | 2 |
| 5-t-C₄H₉ | 2-SC₄H₉ | 1 |
| 5-N(C₂H₅)₂ | 2-SCH₃ | 0 |
| 5-OC₂H₅ | 2-S-i-C₆H₁₃ | 2 |
| 5-Cl | 2-S-cyclohexyl | 1 |
| 5-CF₃ | 2-SCH₃ | 0 |
| 5-OH | 2-S-cyclopentyl | 0 |
| 5-CN | 2-SC₅H₁₁ | 1 |
| 5-NO₂ | 2-S-t-C₄H₉ | 1 |
| 5-COOH | 2-SC₃H₇ | 2 |
| 5-C(O)NHC₃H₇ | 2-SC₂H₅ | 1 |
| 5-C(O)OC₃H₇ | 2-SCH₃ | 0 |
| 5-C(O)ONa | 2-SH | 2 |
| 5-C(O)N-cyclohexyl | 2-SC₂H₅ | 1 |
| 4-F | 2-S-cyclohexyl | 1 |
| 4-CH₃ | 2-S-cyclopentyl | 2 |
| 4-OC₃H₇ | 2-SC₆H₁₃ | 2 |
| 4-CN | 2-S-i-C₄H₉ | 1 |
| 4-CF₃ | 2-SC₂H₅ | 0 |
| 4-C(O)OCH₃ | 2-SCH₃ | 0 |
| 5-N-piperidinyl | 2-S-i-C₃H₇ | 2 |
| 2-Br | 4-SH | 1 |
| 2-C₄H₉ | 4-SCH₃ | 1 |
| 2-NO₂ | 4-SC₂H₅ | 0 |
| 2-OH | 4-S-i-C₃H₇ | 2 |
| 5-CN | 4-S-t-C₄H₉ | 2 |
| 5-CF₃ | 4-SC₅H₁₁ | 2 |
| 5-C(O)OH | 4-SC₆H₁₃ | 1 |
| 5-C(O)N(C₄H₉)(C₂H₅) | 4-S-cyclopentyl | 1 |
| 6-C(O)N-piperidinyl | 4-S-cyclohexyl | 1 |
| 6-C₅H₁₁ | 4-SC₂H₅ | 1 |
| 6-C(O)OC₂H₅ | 4-SC₄H₉ | 1 |
| 6-NH₂ | 4-SC₃H₇ | 2 |
| 2-H | 5-SH | 0 |
| 2-C₄H₉ | 5-SCH₃ | 2 |
| 2-OCH₃ | 5-SC₂H₅ | 2 |
| 2-CN | 5-SC₃H₇ | 1 |
| 2-CF₃ | 5-S-t-C₄H₉ | 0 |
| 2-NO₂ | 5-S-i-C₅H₁₁ | 2 |
| 2-OH | 5-S-2,2-dimethylbutyl | 1 |
| 2-Br | 5-S-cyclopentyl | 1 |
| 2-F | 5-S-cyclohexyl | 2 |
| 2-COOH | 5-SC₂H₅ | 1 |
| 2-C(O)N(C₆H₁₃)(CH₃) | 5-SH | 2 |
| 2-C(O)N-pyrrolidinyl | 5-SCH₃ | 0 |
| 2-Cl | 5-SC₂H₅ | 0 |
| 2-CN | 5-S-i-C₃H₇ | 2 |
| 4-C₂H₅ | 5-S-t-C₄H₉ | 2 |
| 4-OCH₃ | 5-S-neopentyl | 1 |
| 4-I | 5-SC₆H₁₃ | 1 |
| 4-CN | 5-SCH₃ | 1 |
| 4-CF₃ | 5-SCH₃ | 0 |
| 4-COCH₃ | 5-SC₂H₅ | 1 |
| 4-C(O)NH₂ | 5-SC₃H₇ | 2 |
| 4-N(CH₃)₂ | 5-SCH₃ | 1 |

TABLE IV

[Structure: benzene ring with H-N-C(=O)-C(=O)-OR groups at positions, Y substituent, and S(O)$_n$R$_1$ group]

R is ethyl

| Y | SR | n |
|---|---|---|
| 3—C(=O)—N(piperidinyl) | 2-SH | 2 |
| 3—C(=O)—OH | 2-SC$_2$H$_5$ | 0 |
| 3-CF$_3$ | 2-S-i-C$_4$H$_9$ | 1 |
| 3-Br | 2-SC$_6$H$_{13}$ | 0 |
| 3-H | 2-S-cyclohexyl | 2 |
| 3-CH$_3$ | 2-S-cyclobutyl | 2 |
| 3-OC$_2$H$_5$ | 2-S-cyclohexyl | 2 |
| 3-NO$_2$ | 2-SCH$_3$ | 1 |
| 5-t-C$_4$H$_9$ | 2-SC$_3$H$_7$ | 1 |
| 5-OCH$_3$ | 2-S-i-C$_5$H$_{11}$ | 0 |
| 5-OH | 2-S-cyclohexyl | 1 |
| 5-F | 2-S-cyclohexyl | 2 |
| 5-C$_2$H$_5$ | 2-S-cyclobutyl | 1 |
| 5-CN | 2-S-neopentyl | 2 |
| 5-i-C$_3$H$_7$ | 2-S-i-C$_3$H$_7$ | 0 |
| 5—CN(i-C$_6$H$_{13}$)(CH$_3$) | 2-SC$_2$H$_5$ | 0 |
| 6-Cl | 2-SCH$_3$ | 1 |
| 6-OH | 2-SH | 2 |
| 6-CH$_3$ | 2-S-cyclohexyl | 1 |
| 6-CN | 2-S-cyclobutyl | 2 |
| 6-OC$_3$H$_7$ | 2-SC$_3$H$_7$ | 1 |
| 6—C(=O)—OH | 2-SC$_4$H$_9$ | 1 |
| 6-NO$_2$ | 2-S-cyclohexyl | 1 |
| 6—C(=O)NHCH$_3$ | 2-SCH$_3$ | 0 |

TABLE V

The compounds of Tables II, III and IV are transesterified to produce compounds wherein R is methyl, propyl, butyl, pentyl, hexyl, heptyl, octyl, phenyl, benzyl, or phenethyl.

TABLE VI

The compounds of Tables II, III, IV and V are hydrolyzed to produce compounds wherein R is hydrogen.

TABLE VII

The compounds of Table VI are converted to physiologically acceptable metal or amine salts, that is, compounds wherein R is a metal or amine cation, by standard techniques. Preferred are compounds wherein R is sodium or tris(hydroxymethyl)aminomethane.

Tables V, VI and VII are not drafted in the same manner as Tables II, III and IV for the purpose of conciseness. However, the same illustrative scoping is intended.

The following examples are compounds in accordance with this invention.

Example 1 Ethyl 3'-(methylthio) oxanilate

A mixture of 3-methylmercaptoaniline (10 g., 0.072 moles) and diethyl oxalate (75 ml) is heated at reflux for three hours. A white solid (8.3 g.) is isolated by filtration. Recrystallization from ethanol gives a white solid (7.2 g.). A second crop is isolated from the reaction mixture as a white solid after recrystallization. Total yield 12.6 g. (mp 103°-105°, 46%).

Analysis Calc'd for: C$_{11}$H$_{13}$NO$_3$S: C, 55.21; H, 5.47; N, 5.85; S, 13.40: Found: C, 55.77; H, 5.46; N, 6.13; S, 14.27;

uv (EtOH) $\lambda_{max}$ ($\epsilon$): 257 m$\mu$ (5,800)

ir (Nujol): NH 3320, 3290; =CH 3060; C=O 1720, 1710, 1700sh; C=O/C=N/C=C NH$_{def}$ 1675, 1600, 1580, 1545, 1515, 1485 C-O/CN-other 1290, 1180, 1025, 775, 715 cm$^{-1}$ Example 2 Ethyl 3'-(Methylsulfinyl)oxanilate (peroxybenzoic acid route)

m-Chloroperoxybenzoic acid (0.85 g., 0.0042 mole) in cold methylene chloride (10 ml.) is added dropwise to a cold (ice bath) solution of ethyl 3'-(methylthio)oxanilate (1.0 g., 0.0042 mole) in methylene chloride (50 ml.). The reaction mixture is stirred in an ice bath for one hour. A solution of sodium bisulfite (1.0 g. in 100 ml. H$_2$O ) is added to the reaction mixture and the mixture extracted with CH$_2$Cl$_2$ (3 × 50 ml.). The combined organic phases are washed with water, dried with anhydrous sodium sulfate and the solvent removed. The residue is recrystallized from Shellysolve B-benzene to give a white solid (0.45 g., m.p. 130°-131°, 42%). Thin layer chromatography (silica gel, 1% MeOH in HCCl$_3$) showed slight contamination by the sulfone.

nmr (CDCl$_3$): 1.4 δ (3H, t, CH$_3$), 2.8 δ (3H, s,

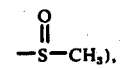
—S(=O)—CH$_3$).

4.5 δ (2H, q, —CH$_2$—), 7.3 — 8.2 δ (4H, mult. aromatic H), 9.7 δ (1H, s broad, NH).

Example 3 Ethyl 3'-(Methylsulfinyl)oxanilate (periodate route)

A solution of ethyl 3-(methylthio)oxanilate (4.0 g., 0.0167 mole) in dioxane-water (1:1, 80 ml.) is added to 0.5 M aqueous sodium metaperiodate (45 ml.). The reaction mixture is stirred at room temperature for one and one-half hours and then extracted with $CH_2Cl_2$ (3 × 100 ml.). The combined $CH_2Cl_2$ extracts are washed with water, followed by 0.7 M sodium bisulfite solution (2 × 100 ml.). The organic phase is dried with sodium sulfate. Removal of the solvent leaves a white solid (3.05 g., 71%). Recrystallization from Skellysolve B-benzene gives a white solid (mp 128°–130°).

Analysis Calc'd for: $C_{11}H_{13}NO_4S$: C, 51.75; H, 5.13; N, 5.49; S, 12.56: Found: C, 51.96; H, 5.16; N, 5.52; S, 12.96;

uv (EtOH) $\lambda_{max}$ ($\epsilon$): 245 m$\mu$ (10,250), 260 (10,250)
ir (Nujol): NH 3170, 3120; NH/=CH 3040;

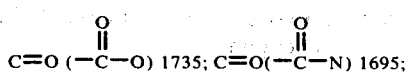

C=O (—C—O) 1735; C=O(—C—N) 1695;

C=C/amide II 1595, 1545; C—C/C—N 1280 1235, 1185;

—S—/C=O/other 915, aromatic CH other 785, 685cm$^{-1}$
nmr ($CDCl_3$): 1.4 $\delta$ (3H, t, —$CH_3$), 2.8 $\delta$ (3H, s,

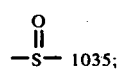

SCH$_3$), 4.4 $\delta$ (2H, q, —$CH_2$—), 7.2–8.2 $\delta$ (4H, multiplet, aromatic H), 9.7 $\delta$ (1H, s broad, NH).

Example 4 3'-(Methylsulfinyl)oxanilic Acid

Ethyl 3'-(methylsulfinyl)oxanilate (0.50 g., 0.002 mole) is dissolved in 1.0 N sodium hydroxide (2ml.). The reaction mixture is stirred ten minutes at room temperature. 1.0 M hydrochloric acid (3 ml.) is added to the reaction mixture to give a white solid (0.40 g.). Recrystallization from methanol gives a white solid (0.28 g., mp 225°, 63%).

Analysis Calc'd for: $C_9H_9NO_4S$: C, 47.57; H, 3.99; N, 6.17; S, 14.11; Found: C, 47.44; H, 4.12; N, 6.11; S, 14.32 uv (EtOH) $\lambda_{max}$ ($\epsilon$): 248 sh (12,550), 256 (12,800) m$\mu$
ir (Nujol): NH/acid OH 3240, 3160, 3060; C=O acid 1715; C=O amide/C=C/amide II 1600, 1560; 1480; C—N/C—O 1350, 1315, 1300;

$$-\overset{O}{\underset{\|}{S}}-\ 1035;$$

Aromatic CH 785, 685cm$^{-1}$
nmr (DMSO-d$_6$): 2.7 (3H, s,

SCH ), 7.3–8.3 (5H, multiplet, aromatic H and $CO_2H$), 11 $\delta$ (1H, s broad, NH).

Example 5 Ethyl 3'-(methylsulfonyl)oxanilate

A solution of m-chloroperoxybenzoic acid (2.55 g., 0.0148 mole) in cold $CH_2Cl_2$ is added to a solution of ethyl 3'-(methylthio)oxanilate (1.0 g.) in cold $CH_2Cl_2$. The reaction mixture is stirred at 0° for one hour. An aqueous solution of sodium bisulfate (1.0 g. in 100 ml.) is added to the reaction mixture. The mixture is extracted with methylene chloride (3 × 75 ml.). The combined extracts are washed with water (1 × 50 ml.) and dried with anhydrous sodium sulfate. Removal of the solvent leaves a white solid (1.54 g., mp 133°–135°). The solid is dissolved in $CH_2Cl_2$ and washed with saturated aqueous sodium bicarbonate (2 × 50 ml.). The organic phase is dried with anhydrous sodium sulfate. Removal of the solvent leaves a solid. Recrystallization from Skellysolve B-benzene gives a white solid (0.59 g., mp 143°–145°, 52%).

Analysis Calc'd for: $C_{11}H_{13}NO_5S$: C, 48.70; H, 4.83; N, 5.16; S, 11.82; Found: C, 48.36; H, 4.62; N, 5.05; S, 11.89 ir (Nujol): NH 3320; =CH 3060; C=O ester 1730; C=O amide 1700; C=C 1595, 1490; Amide II 1545; $SO_2$/C—O/C—N 1310, 1300, 1230, 1185, 1145, other 960, aromatic CH/other 770, 715, 680cm$^{-1}$
nmr ($CDCl_3$): 1.5 $\delta$ (3H, t, —$CH_3$); 3.2 $\delta$ (3H, s, $SO_2CH_3$), 4.5 $\delta$ (2H, q, $CH_2$), 7.4–8.4 $\delta$ (3H, multiplet, aromatic H), 9.4 $\delta$ (1H, s broad, NH).

Example 6 3'-(Methylsulfonyl)oxanilic Acid

Ethyl 3'-(methylsulfonyl)oxanilate (0.30 g., 0.0011 mole) is stirred in 1.0 N sodium hydroxide solution (4 ml.) until solution is complete (ca. 10 min.). 1.0 N hydrochloric acid (4 ml.) is added. The resulting solid is collected and recrystallized from methanol to give a white crystalline solid (200 mg., mp 230°–231°, 74%).

Analysis Calc'd for: $C_9H_9NO_5S$: C, 44.44; H, 3.73; N, 5.76; S, 13.18; Found: C, 44.61; H, 3.88; N, 5.71; S, 13.10 uv (EtOH): 258 (11,450) m$\mu$
ir (Nujol): NH/acid OH 3270, 3230, 3000 broad; C=O (acid) 1770, C=O (amide) 1695; C=C 1600, 1480; amide II 1558; C—C/C—N/$SO_2$— 1350, 1320, 1310, 1295, 1210, 1180, 1145; other 970; aromatic CH 775, 680cm$^{-1}$

Example 7 Diethyl N,N'-(2-chloro-5-methylthio-m-phenylene)dioxamate a. 4-(Methylthio)-2,6-dinitrophenol A solution of 4-(methylthio)phenol (5 g.) in glacial acetic acid (10 ml.) is added to a cold solution of glacial acetic acid (75 ml.) and conc. nitric acid (25 ml.). The mixture is poured into water after stirring one hour at 5° C. The resulting solid is collected by filtration.

b. 1-Chloro-4-(methylthio)-2,6-dinitrobenzene

A mixture of 4-(methylthio)-2,6-dinitrophenol (1 g.), phosphorus oxychloride (7.5 ml.), and dimethylformamide (1 ml.) is heated at 90°–100° C. for four hours. The cooled reaction mixture is poured into ice-water. The resulting product is collected by filtration.

c. 2-Chloro-5-methylthio-1,3-phenylenediamine

A mixture of 1-chloro-4-(methylthio)-2,6-dinitrobenzene (1.0 g.), 5% platinum-on-charcoal sulfided (Greenfield) catalyst (100 mg.) and methanol is treated with hydrogen (500 psi) until hydrogen uptake stops. The catalyst is removed by filtration. Removal of the solvent leaves the diamine.

d. Diethyl N,N'-(2-chloro-5-methylthio-m-phenylene)-dioxamate

A mixture of 2-chloro-5-methylthio-1,3-phenylenediamine (1.0 g.), triethylamine (1.2 g.), and ethyl oxalylchloride (1.5 g.) in dimethylformamide are stirred at room temperature for twenty-four hours. The reaction mixture is poured into water and the desired dioxamate collected by filtration.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by method known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane (Freon 114), trichloromonofluoromethane (Freon 11), dichloromonofluoromethane (Freon 21), monochlorodifluoromethane (Freon 22), trichlorotrifluoroethane (Freon 113), difluoroethane (Genetron 142-A) and monochlorotrifluoromethane (Freon 13).

The term "unit dosage form", as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 1 to about 40 mg. of compound in a single dose, administered parenterally or by inhalation in the compositions of this invention are effective for preventing allergy attacks. More specifically, the single dose is from about 2 to about 35 mg. of compound. The oral and rectal dose is from about 5 to about 75 mg. in a single dose. More specifically, the single dose is from about 10 to about 40 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 10 mg. of the tris-(hydroxymethyl)aminomethane salt of 3'-(methylsulfinyl)-oxanilic acid. Four hours later, the individual insufflates 0.2 mg. of the same compound and every four to six hours thereafter insufflates 0.2 mg. of the same compound until effective asthma prophylaxis is not provided. The individual then insufflates 10 mg. of the same compound, then reduces the insufflation dosage fo 0.2 mg. four to six hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

Example 8

A lot of 10,000 tablets, each containing 50 mg. of ethyl 3'-(methylsulfinyl)oxanilate is prepared from the following types and amounts of ingredients:

| | | |
|---|---|---|
| Ethyl 3'-(methylsulfinyl)- oxanilate | 500 | Gm. |
| Dicalcium phosphate | 1,000 | Gm. |
| Methylcellulose, U.S.P. (15 cps) | 60 | Gm. |
| Talc | 150 | Gm. |
| Corn starch | 200 | Gm. |
| Magnesium stearate | 10 | Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four to six hours.

Example 9

One thousand two-piece hard gelatin capsules, each containing 50 mg. of ethyl 3'-(methylsulfinyl)-oxanilate are prepared from the following types and amounts of ingredients:

| | | |
|---|---|---|
| Ethyl 3'-(methylsulfinyl)- oxanilate | 50 | Gm. |
| Talc | 150 | Gm. |
| Magnesium stearate | 1 | Gm. |

The ingredients are mixed well and filled into capsules of the proper size.

Capsules so prepared are useful in preventing attacks of bronchial asthma at a dose of one capsule every four to six hours.

Example 10

One thousand tablets, each containing 10 mg. of ethyl 3'-(methylsulfinyl)oxanilate are prepared from the following types and amounts of ingredients:

| | | |
|---|---|---|
| Ethyl 3'-(methylsulfinyl)- oxanilate | 10 | Gm. |
| Microcrystalline cellulose NF | 410 | Gm. |
| Starch | 100 | Gm. |
| Magnesium stearate powder | 3 | Gm. |

The ingredients are screened and blended together and pressed into tablets.

The tablets are useful to protect against food allergy at a dose of one tablet before meals.

Example 11

One thousand tablets, each containing 20 mg. of diethyl N,N'-(2-chloro-5-methylthio-m-phenylene)dioxamate are prepared from the following types and amounts of ingredients:

Diethyl N,N'-(2-chloro-5-methyl-

| | | |
|---|---:|---|
| thio-m-phenylene)dioxamate | 20 | Gm. |
| Microcrystalline cellulose NF | 410 | Gm. |
| Starch | 100 | Gm. |
| Magnesium stearate powder | 3 | Gm. |

The ingredients are screened and blended together and pressed into tablets.

The tablets are useful to protect against food allergy at a dose of one tablet before meals.

Example 12

A sterile preparation suitable for intramuscular injection and containing 20 mg. of tris(hydroxymethyl)aminomethane salt of 3'-(methylsulfinyl)oxanilic acid in each milliliter is prepared from the following ingredients:

| | | |
|---|---:|---|
| Tris(hydroxymethyl)aminomethane salt of 3'-(Methylsulfinyl)-oxanilic acid | 20 | Gm. |
| Benzyl benzoate | 200 | ml. |
| Methylparaben | 1.5 | Gm. |
| Propylparaben | 0.5 | Gm. |
| Cottonseed oil q.s. | 1,000 | ml. |

One milliliter of this sterile preparation is injected for prophylactic treatment of allergic rhinitis.

Example 13

Six hundred ml. of an aqueous solution containing 5.0 mg. of the tris(hydroxymethyl)aminomethane salt of N,N'-(2-chloro-5-methylthio-m-phenylene)dioxamic acid per ml. is prepared as follows:

| | | |
|---|---:|---|
| Tris(hydroxymethyl)aminomethane salt of N,N'-(2-chloro-5-methylthio-m-phenylene)dioxamic acid | 3 | Gm. |
| Sodium chloride | 5 | Gm. |
| Water for injection q.s. | 600 | ml. |

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every four to six hours for prevention of asthmatic attacks.

Example 14

A powder mixture consisting of 2 grams of sodio 3'-(methylsulfinyl)oxanilate and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

Example 15

Twelve grams of an aerosol composition are prepared from the following ingredients:

| | | |
|---|---:|---|
| Tris(hydroxymethyl)aminomethane salt of 3'-(methylsulfinyl)- | | |
| oxanilic acid | 1.00 | Gm. |
| Freon 12 | 1.44 | Gm. |
| Freon 114 | 2.16 | Gm. |
| Water | 6.80 | Gm. |
| Sorbitan monoleate | 0.60 | Gm. |

The THAM salt is dissolved in the water and chilled to $-30°$ C. and added to the chilled Freons. The twelve grams of compositions are added to a 13 cc plastic coated bottle and capped with a metering valve. The metering valve releases 80 mg. of composition in an aerosol. The aerosol is inhaled every four to six hours for prevention of asthmatic attacks.

Example 16

In individuals who require continual treatment in the Examples 8 through 15, the dosage of the Example is given initially and each succeeding administration of the drug is at 1/50 of the initial dosage. This maintenance dosage is continued until effective allergy prophylaxis is not obtained. The initial dosage of Examples 8 through 15 is then started once more, followed by the maintenance dosages.

Example 17

After allowing for the different solubilities of the compounds and the activity of the particular compound as measured, for example, by the in vivo rat passive cutaneous anaphylaxis assay, a suitable quantity of each of the compounds of Table II through Table VII and Examples 1–7, is substituted for the active compound in the compositions and uses of Examples 8 through 15. Results showing anti-allergy activity are obtained.

Example 18

The rat passive cutaneous anaphylaxis assay is run in the following manner

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The tris(hydroxymethyl)aminomethane salt of 3'-(methylsulfinyl)oxanilic acid is prepared by dissolving the acid in an equivalent weight of aqueous tris(hydroxymethyl)aminomethane and is tested in the rat passive cutaneous anaphylaxis assay in the above manner.

The inhibitory dose$_{50}$ for the tris(hydroxymethyl)aminomethane salt of 3'-(methylsulfinyl)oxanilic acid is approximately 2.5 mg./kg. by the intravenous route.

All example temperatures are in degrees Centigrade.
We claim:

1. A compound of the formula

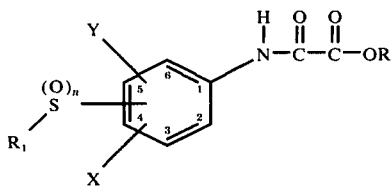

wherein X is at the 3 or 4 position and is hydrogen or

Y is selected from the group consisting of hydrogen, alkyl of one to four carbon atoms, inclusive, halo, hydroxy, cyano, nitro, trifluoromethyl,

wherein D is selected from the group consisting of hydrogen, and a physiologically acceptable metal or amine cation, R is selected from the group consisting of hydrogen, and a physiologically acceptable metal or amine cation;

$R_1$ is selected from the group consisting of hydrogen, alkyl of one to six carbon atoms, inclusive, and cycloalkyl of five or six carbon atoms, inclusive; and $n$ is 0, 1 or 2.

2. A compound in accordance with claim 1 wherein Y is selected from the group consisting of hydrogen, alkyl of one to three carbon atoms, inclusive, halo, hydroxy, cyano, nitro, trifluoromethyl,

wherein D is selected from the group consisting of hydrogen, and a physiologically acceptable metal or amine cation.

3. A compound in accordance with claim 2 wherein X is at the 3 position;

Y is selected from the group consisting of hydrogen, alkyl of one to three carbon atoms, inclusive, fluoro, chloro, bromo, cyano, trifluoromethyl, and

and $R_1$ is selected from the group consisting of hydrogen and alkyl of one to four carbon atoms, inclusive.

4. A compound in accordance with claim 3 wherein Y is at the 2 or 5 position;

$R_1S(O)_n$ is at the 2 or 5 position; and

R is selected from the group consisting of hydrogen, and a physiologically acceptable metal or amine cation.

5. A compound in accordance with claim 4 wherein $n$ is zero.

6. A compound in accordance with claim 4 wherein $n$ is one.

7. A compound in accordance with claim 4 wherein $n$ is two.

8. 3'-(methylsulfinyl)oxanilic acid according to claim 1.

9. 3'-(methylsulfonyl)oxanilic acid according to claim 1.

10. A pharmaceutical composition which comprises an anti-allergy effective amount of a compound of the formula

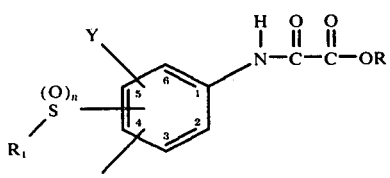

wherein X is at the 3 or 4 position and is hydrogen or

Y is selected from the group consisting of hydrogen, alkyl of one to four carbon atoms, inclusive, halo, hydroxy, cyano, nitro, trifluoromethyl,

wherein D is selected from the group consisting of hydrogen, and a physiologically acceptable metal or amine cation, R is selected from the group consisting of hydrogen,

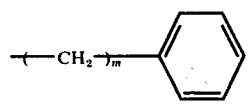

wherein $m$ is 0, 1 or 2, and a physiologically acceptable metal or amine cation;

$R_1$ is selected from the group consisting of hydrogen, alkyl of one to six carbon atoms, inclusive, and cycloalkyl of five or six carbon atoms, inclusive; and $n$ is 0, 1 or 2, in association with a pharmaceutical carrier.

11. A method of prophylactically treating allergy of a reagin or non-reagin mediated nature in a mammal which comprises the administration of an anti-allergy effective amount of a compound of the formula

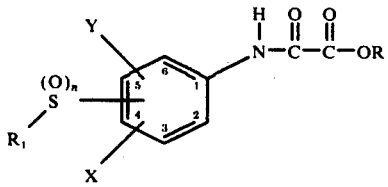

wherein X is at the 3 or 4 position and is hydrogen or

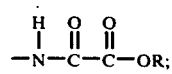

Y is selected from the group consisting of hydrogen, alkyl of one to four carbon atoms, inclusive, halo, hydroxy, cyano, nitro, trifluoromethyl,

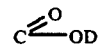

wherein D is selected from the group consisting of hydrogen, and a physiologically acceptable metal or amine cation, R is selected from the group consisting of hydrogen, and a physiologically acceptable metal or amine cation;

$R_1$ is selected from the group consisting of hydrogen, alkyl of one to six carbon atoms, inclusive, and cycloalkyl of five or six carbon atoms, inclusive;

and $n$ is 0, 1 or 2.

12. A method in accordance with claim 11 wherein the compound is in association with a pharmaceutical carrier.

* * * * *